United States Patent [19]

DiGeorge

[11] Patent Number: 4,520,804

[45] Date of Patent: Jun. 4, 1985

[54] DOUBLE-LOCKING RATCHET FOR ORTHOPEDIC BRACE

[76] Inventor: Michael A. DiGeorge, P.O. Box 563, Sulphur, La. 70663

[21] Appl. No.: 289,897

[22] Filed: Aug. 4, 1981

[51] Int. Cl.³ .............................................. A61F 3/00
[52] U.S. Cl. ....................................... 128/80 C; 3/4; 3/26
[58] Field of Search ................. 128/80 R, 80 B, 80 C, 128/80 A, 88; 3/22-26; 74/577 R; 81/10

[56] References Cited

U.S. PATENT DOCUMENTS

| | | | |
|---|---|---|---|
| 294,282 | 2/1884 | Sinclair | 74/577 R |
| 772,318 | 10/1904 | Wenneborg, Jr. | 128/80 F |
| 2,943,622 | 7/1960 | Nelson | 128/80 F |
| 4,323,059 | 4/1982 | Rambert et al. | 128/88 |
| 4,381,768 | 5/1983 | Erichsen et al. | 128/80 C |

Primary Examiner—Richard J. Apley
Assistant Examiner—D. J. Isabella
Attorney, Agent, or Firm—Harvey B. Jacobson

[57] ABSTRACT

A pivotal knee joint associated with an orthopedic leg brace is provided with a ratchet wheel operable to permit adjustable back and forth movement of a knee. Both upper and lower leg brace sections of the leg brace are pivotally attached to the rotatable axis of the ratchet wheel, and a pair of rotatable pawls are provided which are selectively manually operable by a user to effectively control the direction of rotation of the ratchet wheel, as well as to lock the ratchet wheel and the associated leg brace against further rotation or relative pivotal movement. Depending on the positioning of the pawls, various leg muscles may then be exercised and stretched through the relative positioning of the upper and lower leg brace sections, and the knee joint having the double-locking ratchet.

9 Claims, 6 Drawing Figures

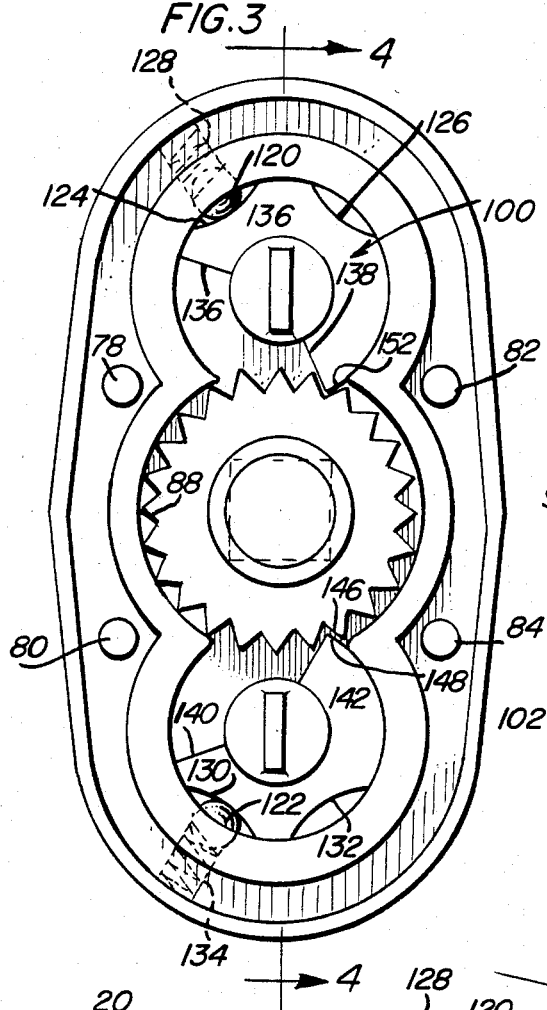
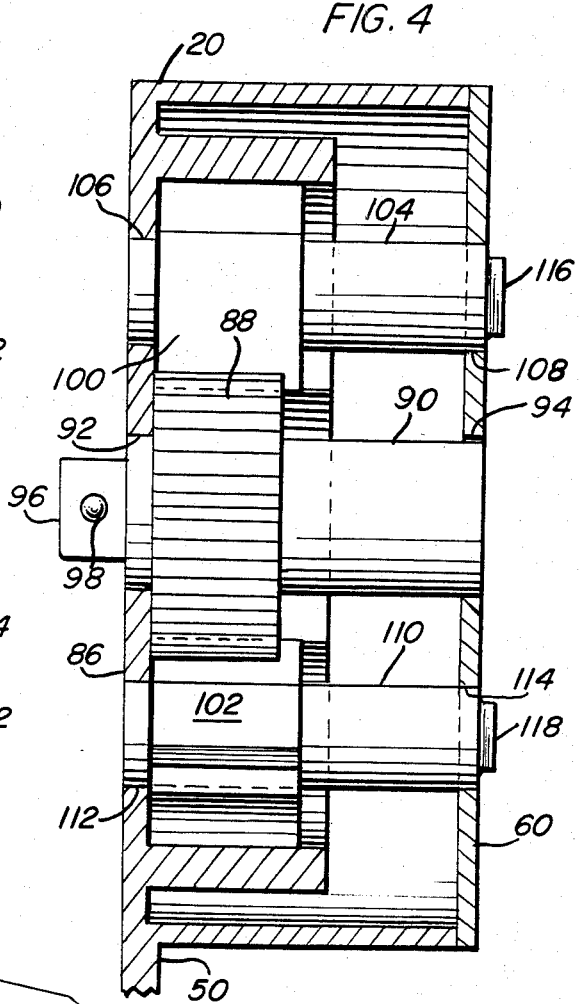
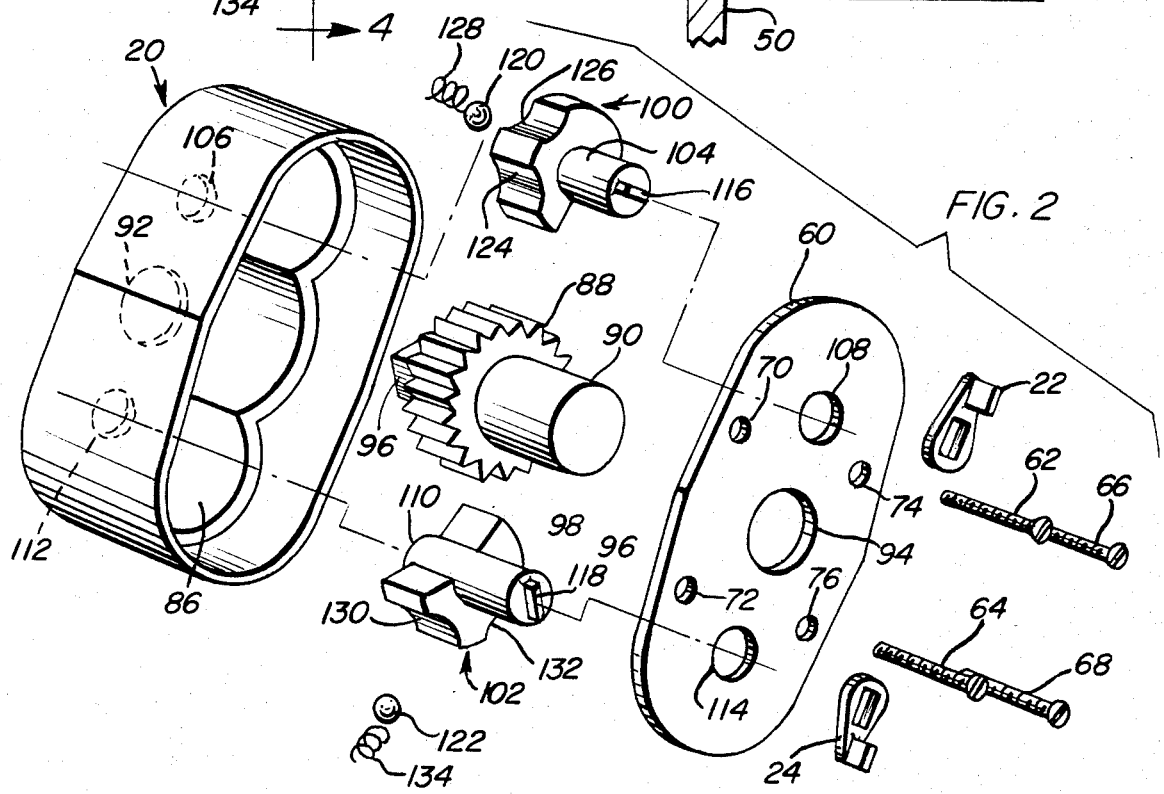

4,520,804

DOUBLE-LOCKING RATCHET FOR ORTHOPEDIC BRACE

BACKGROUND OF THE INVENTION

1. Field of the Invention

The present invention relates generally to orthopedic braces and more particularly pertains to a new and improved knee joint for an orthopedic brace which permits relative pivotal movement and fixed positioning between upper and lower leg support members and the knee joint, thereby to selectively stretch various leg muscles.

2. Description of the Prior Art

It is well known in the art that persons needing and using orthopedic leg braces usually do not possess sufficient muscular strength and control to hold the braced legs rigid and straight in a weight supporting capacity while walking. In this respect, considerable attention has been directed to developing leg braces having pivotal knee joints with locks that prevent such pivotable movement whenever the weight of the user is placed on the braced leg. However, these prior art devices have usually been quite complicated in structure and in many cases, they have proven to be inefficient and unreliable. Additionally, those of a complicated structure are subject to frequent malfunction and excessive wear, in addition to being relatively expensive to produce and difficult to put on and take off of a leg.

For example, U.S. Pat. No. 2,632,440, issued to Hauser et al. on Mar. 24, 1953, discloses a leg brace joint and lock which comprises a thigh section and a leg section, each being reinforced with a suitable number of bands encircling the thigh and leg of a user. The thigh and leg sections are interconnected by a double joint which follows the normal bending action of the knee joint of the leg, while control of relative movement between the brace sections is effected by the provision of various types of locking instrumentalities fixedly locatable in predetermined positions, thereby to effect a desired control of the double joint. However, the construction of the Hauser et al. device is quite complicated, and no simple and efficient means is provided for changing the pivotal movement between the upper and lower leg sections relative to the knee joint. Accordingly, it can be appreciated that there exists a continuing need for new and improved orthopedic leg braces which employ adjustable knee joints in a manner whereby a user can quickly and easily alter the relative pivotal movement and positioning between upper and lower leg brace sections and the knee joint associated therewith. In this connection, the present invention substantially fulfills this need.

SUMMARY OF THE INVENTION

The general purpose of the present invention, which will be described subsequently in greater detail, is to provide a new and improved locking knee joint for orthopedic braces which has all of the advantages of the prior art locking knee joints and none of the disadvantages. To attain this, the double-locking ratchet knee joint forming the present invention is pivotally connectible between upper and lower leg support or brace sections associated with a conventional orthopedic leg brace, and through the use of a pair of manually actuatable locking levers, relative pivotal movement between the knee joint and the upper and lower leg sections is controllably permitted. Specifically, the upper and lower leg sections of a conventional orthopedic brace are fixedly attachable to the rotatable shaft of the ratchet wheel and a pair of rotatable locking pawls are provided which may be selectively moved into and out of engagement with the ratchet wheel, thereby to control both the clockwise and counterclockwise rotation of the wheel as desired. When both locking pawls are in engagement with the ratchet wheel, no pivotal movement is permitted between the upper and lower leg sections. Counterclockwise movement of the ratchet wheel is permitted when the upper locking pawl is taken out of locking engagement with the wheel with the lower locking pawl remaining in engagement, and clockwise movement of the wheel is permitted when the lower pawl is out of engagement and the upper pawl is in engagement. With one pawl engaged and the other disengaged, the ratchet wheel can move freely only in one direction, thereby to prevent a return of the associated leg brace sections to their original positions until both locking pawls are disengaged from the wheel.

It is, therefore, an object of the present invention to provide a new and improved double-locking ratchet knee joint for orthopedic braces that has all the advantages of similarly employed prior art orthopedic brace knee joints and none of the disadvantages.

It is another object of the present invention to provide a new and improved double-locking ratchet knee joint for orthopedic braces which may be easily and economically manufactured.

It is a further object of the present invention to provide a new and improved double-locking ratchet knee joint for orthopedic braces which is both simple in construction and limited in the number of moving parts.

Still another object of the present invention to provide a new and improved double-locking ratchet knee joint for orthopedic braces which is efficient and reliable in its operation.

Yet another object of the present invention to provide a new and improved double-locking ratchet knee joint for orthopedic braces which is durable and rugged in its construction.

Even another object of the present invention to provide a new and improved double-locking ratchet knee joint for orthopedic braces which provides in the apparatus of the prior art some features as a result of which the proper advantages will be retained and even improved, while bringing thereto remedies for existing inconveniences.

A still further object of the present invention to provide a new and improved double-locking ratchet knee joint for orthopedic braces which may be easily maintained and which is readily adaptable and attachable to existing conventional orthodpedic leg braces.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 2 is an exploded perspective view illustrating the basic construction and manner of assembly of the present invention.

FIG. 3 is a detailed plan view of the present invention illustrating the components thereof in an assembled construction.

FIG. 4 is transverse cross-sectional view of the present invention taken along the line 4—4 in FIG. 3.

DESCRIPTION OF THE PREFERRED EMBODIMENT

Figure 1:
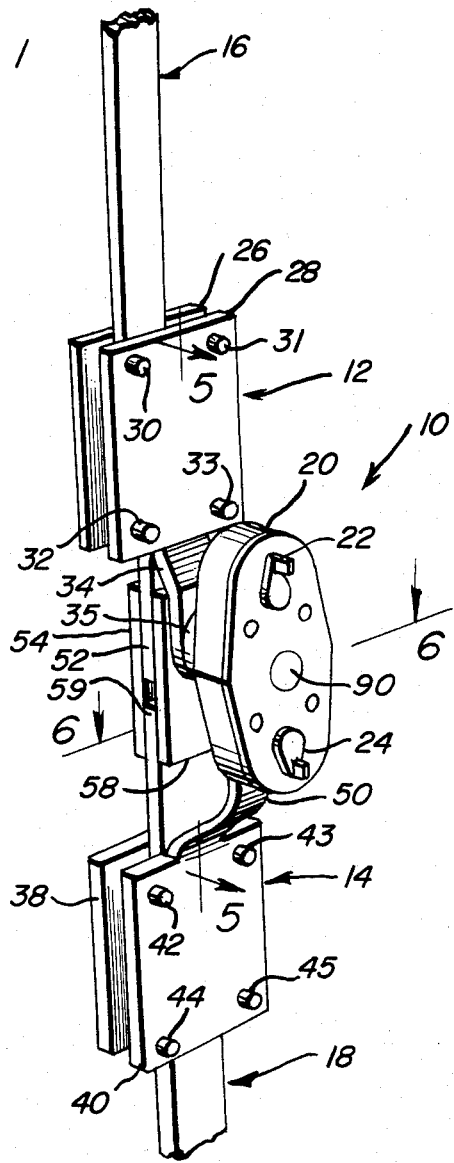
FIG. 1 is a perspective view of the double-locking ratchet knee joint for orthopedic braces forming the present invention operably attached between upper and lower leg brace members associated with a conventional orthopedic brace.
Figure 5:
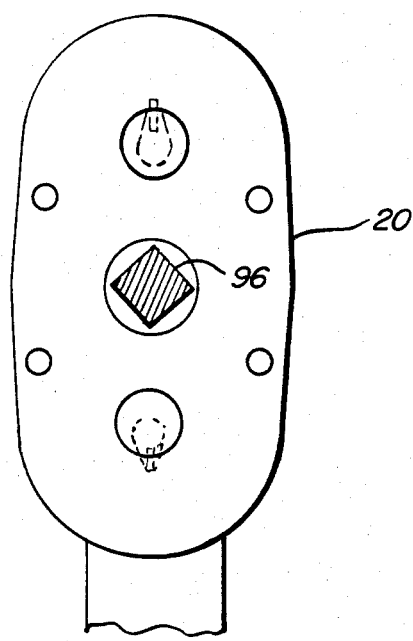
FIG. 5 is longitudinal cross-sectional view taken along the line 5—5 in FIG. 1.

With reference now to the drawings and in particular to FIG. 1 thereof, a double-locking ratchet knee joint for use on orthopedic braces embodying the principles and concepts of the present invention and generally designated by the reference numeral 10 will be described. In this respect, it can be seen that the knee joint 10 includes an upper attachment member 12 and a lower attachment member 14 which are respectively fixedly secured to upper and lower leg brace sections 16, 18. In this regard, the leg brace sections or members 16, 18 form part of a conventional orthopedic brace, while the knee joint 10 forming the present invention is designed to be attached thereto. Further, it can be seen that the upper attachment member 12 and the lower attachment member 14 are respectively fixedly secured to a ratchet wheel housing 20 which includes a pair of locking pawl control levers 22, 24 rotatably mounted on an exterior surface thereof. In effect, the ratchet wheel housing 20 contains the basic operative components of the present invention, with the upper and lower attachment members 12, 14 serving as the means of connecting the housing and its associated components to the conventional leg brace sections 16, 18, respectively. In this regard, the upper attachment member 12 may include a first plate 26 positionable on one side of the leg brace section 16 and a second plate 28 positioned on the opposed side of the leg brace, with the two plates then being attachable together by any conventional attachment means, such as through the use of threaded bolts 30-33. Additionally, the second plate 28 is provided with an integrally attached angulated extension arm 34 which is fixedly securable to a socket 35, the purpose of which will be subsequently described.

Similarly, the lower attachment member 14 may include a first connection plate 38 positioned on one side of the leg brace section 18 and a second connection plate 40 positioned on the opposite side, with further conventional attachment means being employed to join the first and second plates together, such as threaded bolts 42-45. Further, an integral angulated extension arm 50 is provided on one edge of the second plate 40, such arm being fixedly securable to the housing 20 on a lowermost portion thereof.

With respect to the construction of the double-locking ratchet assembly forming a part of the present invention, reference is next made to FIG. 2 of the drawings, wherein an exploded view of the associated components thereof is provided. In this regard, it can be seen that the ratchet wheel housing 20 has a removable side plate 60, such side plate being normally securable to the housing through the use of a plurality of threaded attachment means, such as screws 62, 64, 66, 68, which are directable respectively through the apertures 70, 72, 74, 76 contained in the side plate and then are respectively threadably engageable with apertures 78, 80, 82, 84 positioned in a back wall 86 of the housing 20 as shown in FIG. 3.

As can be clearly ascertained with reference to FIGS. 2-4 of the drawings, a ratchet wheel 88 is centrally positionable within the housing 20 and includes a bearing shaft 90 extending outwardly from opposed sides of the ratchet wheel, such bearing shaft being rotatably and supportably mountable within apertures 92, 94 contained respectively on the back wall 86 and the side plate 60. Additionally, a square-shaped extension 96 is integrally attached to one end of the bearing shaft 90, such extension being provided with a locking ball 98 on one planar surface thereof.

Further provided within the housing 20 are first and second rotatable locking pawls 100, 102 which are rotatably mountable on diametrically opposed sides of the ratchet wheel 88. Specifically, the locking pawl 100 has a bearing support shaft 104 extending outwardly on opposed sides thereof, such shaft being rotatably and supportably mountable within apertures 106, 108 respectively contained on the walls 86, 60. By the same token, locking pawl 102 is provided with a bearing support shaft 110 extending outwardly from opposed sides thereof, such shaft being rotatably and supportably mountable within apertures 112, 114 respectively contained on the walls 86, 60. Further, the ends of the bearing shafts 104, 110 extending outwardly through the apertures 108, 114, respectively, are provided with respective rectangularly shaped extensions 116, 118 to which are respectively mountable the aforementioned locking pawl control levers 22, 24.

Also illustrated in FIGS. 2 and 3 is the use of positioning balls 120, 122 respectively associated with the locking pawls 100, 102. In this connection, the locking pawl 100 is provided with a pair of curvilinear indentations 124, 126, with the positioning ball 120 being selectively positionable in one or the other of the indentations and being substantially retained therein through the use of a spring 128. Similarly, the locking pawl 102 is provided with curvilinear indentations 130, 132 into one of which the positioning ball 122 is selectively positioned while being retained therein by a spring 134.

With particular reference to FIGS. 3-6 of the drawings, the assembled construction of the present invention and its manner of operation will be described. In this respect, it can be seen that the locking pawl 100 is provided with a pair of planar surfaces 136, 138 while similarly, the locking pawl 102 is provided with planar surfaces 140, 142. As most clearly illustrated in FIG. 3, the surface 138 associated with the locking pawl 100 is engageable with the ratchet wheel 88 when the pawl is in its locked position. Similarly, the surface 142 associated with the locking pawl 102 is engageable with the ratchet wheel 88 when this particular pawl is in its locked position. The locked position of locking pawl 100 is defined by the positioning ball 120 being located in the curvilinear indentation 124, while the locked position of locking pawl 102 is defined by the positioning ball 122 being spring biasedly contained within the curvilinear indentation 130. By the same token, it is to be understood that the respective locking pawls 100, 102 will be in their unlocked positions when the positioning balls 120, 122 are contained respectively in the curvilinear indentations 126 and 132 due to a respective rotation of the associated locking pawls effected by a user. Additionally, though not specifically illustrated in the drawings, when the locking pawls 100, 102 are in their unlocked positions, none of the planar surfaces 136, 138, 140, 142 will be in engagement with the ratchet wheel 88. As will be subsequently described during a discussion of the operation of the present invention, depending upon which locking pawl 100, 102 is in engagement with the ratchet wheel 88, either clockwise or counterclockwise movement of the ratchet wheel will be permitted relative to the leg brace sections 16, 18.

FIG. 4 illustrates the aforedescribed mounting of the ratchet wheel 88 and the locking pawls 100, 102 within the ratchet wheel housing 20. In this regard, it can be seen that when the side plate 60 is fixedly secured to the housing 20, the bearing support shaft 104 associated with the locking pawl 100 will be rotatably and supportably mounted within the apertures 106, 108. Similarly, the rotatable bearing support shaft 110 associated with locking pawl 102 will be rotatably and supportably mounted within the apertures 112, 114, while the ratchet wheel 88 will be rotatably bearingly supported within the apertures 92, 94 by its bearing support shaft 90. By the same token, the square-shaped extension 96 will extend outwardly from the back wall 86 so as to be engageable with the aforementioned socket 35 operably attached to extension arm 34 and as most clearly illustrated in FIG. 6. In this connection, the socket 35 may be fixedly secured to extension arm 34 in any conventional manner, such as by welding or the like.

Figure 6:
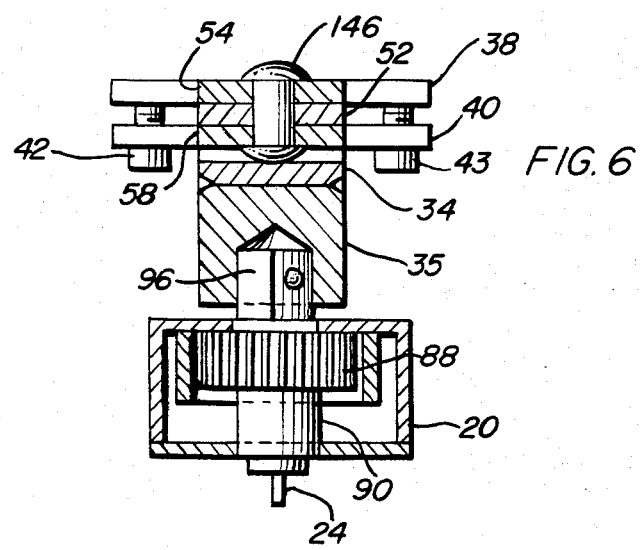
FIG. 6 is a transverse cross-sectional view of the present invention taken along the line 6—6 in FIG. 1.

As to the construction of the conventional leg brace to which the present invention is attachable, reference is made to FIGS. 1 and 6, wherein it can be seen that the conventional existing leg brace includes a connection plate 58 fixedly secured to a topmost portion 59 of the leg brace 18, such connection plate being on one side of the brace 18 with a similar connection plate 54 being fixedly mounted on the opposite side of the brace. A connection pin 146 is fixedly securable between the plates 58, 54 in the manner illustrated, with a lower portion 52 of the leg brace 16 then being rotatably journalled about the pin so as to permit relative pivotal movement between the leg brace sections 16, 18. As shown in FIG. 6, the extension arm 34 overlies pin 146 in an abutting relationship but is not connected thereto.

In operation then, it can be seen that the double-locking ratchet knee joint for orthopedic braces may be selectively attached to existing leg brace sections 16, 18 associated with a conventional orthopedic brace. In this regard, the attachment may be effected by the use of the aforedescribed upper and lower attachment members 12, 14. To permit a rearwardly directed movement of the lower leg of a brace wearer, it can be appreciated that a counterclockwise movement of the ratchet wheel 88 will be required inasmuch as the extension arms 34, 50 are rotatably secured to each other through the ratchet wheel. Such a counterclockwise movement of the ratchet wheel 88 is effected by moving the locking pawl 100 into its unlocked position, i.e., with the positioning ball 120 contained in the curvilinear indentation 126, such unlocked position being effected by a manual rotation of the locking pawl control lever 22. As such, only the surface 142 associated with the locking pawl 102 is in engagement with the ratchet wheel 88. In this connection, reference is made to FIG. 3 of the drawings, wherein the locking pawl 102 is shown in its locked position as above discussed. In this position, it can be seen that a clockwise rotation of the ratchet wheel 88 will be prevented due to the tooth 146 forming part of the ratchet wheel abutting against a back surface 148 of the locking pawl 102. However, restrictive counterclockwise movement of the ratchet wheel 88 is permitted inasmuch as the tooth 150 will bear against the planar surface 142, and the positioning ball 122 will move along the curvilinear indentation 130 due to a compression of its associated spring 134, thereby to permit the tooth 150 to slide past the planar surface 142. Of course, as is well understood by those familiar with the art, this progressive rotation of the teeth of the ratchet wheel 88 over the planar surface 142, with a counter rotation being prevented by the engagement of the surface 148 with the teeth of the ratchet wheel, provides the ratchet construction of the knee joint forming the present invention. In effect, it can be seen that with this arrangement of the locking pawls, i.e., with locking pawl 100 unlocked and locking pawl 102 locked, a continual bending of the user's leg will be permitted, while a subsequent straightening or extension of the leg will not be permitted.

To permit an extension or straightening of the leg, it is only necessary to reverse the operation of the locking pawls 100, 102. Specifically, through an actuation of the locking pawl control lever 22, the locking pawl 100 may be brought back into locking engagement with the ratchet wheel 88, and at the same time, through a manipulation of the locking pawl control lever 24, the locking pawl 102 may be moved into an unlocked position. As such, clockwise rotation of the ratchet wheel 88 will now be permitted inasmuch as the teeth of the wheel will slide past the surface 138 but will be prevented from counterclockwise rotation due to their abutting relationship with the surface 152. As can be further appreciated, once a brace wearer has achieved the desired extension or bending of his leg, he may lockably secure the same in position by bringing both of the locking pawls 100, 102 into locking engagement with the ratchet wheel 88, thereby to prevent both clockwise and counterclockwise relative movement between the leg brace sections 16, 18.

In summary, an orthopedic brace has been described which utilizes a double-locking ratchet knee joint that permits a user to manually control the amount of bending or extending of his leg contained within a brace. Specifically, the ratchet wheel construction of the present invention serves to let a knee joint move in both directions when both locking pawls are disengaged by the locking pawl control levers, and further permits a selective stretching and exercising of selected leg muscles, as well as the gradual straightening or bending of the knee, depending upon the selected fixed securing of the leg brace sections through the manipulation of the respective locking pawls. With respect to the above description then, it should be realized that the optimum dimensional relationships for the parts of the invention are deemed readily apparent and obvious to one who is skilled in the art to which the invention pertains, and all equivalent relationships to those illustrated in the drawings and described in the specification, to include modification of form, size, arrangement of parts and details of operation, are intended to be encompassed by the present invention.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. An improved joint for an orthopedic brace comprising:
   casing means;
   ratchet means substantially contained within said casing means;
   upper leg brace attachment means for fixedly securing said casing means to an upper leg brace associated with said orthopedic brace;
   lower leg brace attachment means for fixedly securing said casing means to a lower leg brace associated with said orthopedic brace; and
   selectably positionable ratchet control means for providing alternative operating characteristics to the joint so as to permit selective pivotal movement between said upper and lower leg braces, said alternative operating characteristics including (a) pivotal movement of the braces in one direction and locking of the braces against pivotal movement in the other direction; (b) pivotal movement of the braces in said other direction and locking of the braces against pivotal movement in said one direction; (c) pivotal movement of the braces both in said one direction and in said other direction; and, (d) locking of the braces against pivotal movement both in said one direction and in said opposite direction, wherein said ratchet means includes a ratchet wheel and said ratchet control means includes first and second pawl means selectively engageable with said ratchet wheel to effectively control said operating characteristics.

2. The improved joint for an orthopedic brace as defined in claim 1, wherein said first and second pawl means are rotatably mounted in said casing means.

3. The improved joint for an orthopedic brace as defined in claim 2, and further wherein said first pawl means is manually controllable by a first lever means positioned on an exterior surface of said casing means and said second pawl means is manually controllable by a second independently operable lever means on the exterior surface of the casing means.

4. The improved joint for an orthopedic brace as defined in claim 1, and further wherein said first and second pawl means are provided with position retaining means.

5. The improved joint for an orthopedic brace as defined in claim 4, wherein said position retaining means includes spring biased balls receivable within curvilinear indentations positioned on said first and second pawl means.

6. The improved joint for an orthopedic brace as defined in claim 5, wherein said curvilinear indentations permit limited rotatable movement of said first and second pawl means in the one and other directions of rotation, so as to permit said ratchet wheel to move past said first and second pawls when a desired direction of rotation of said ratchet wheel has been selected.

7. An improved joint for an orthopedic brace comprising:
   casing means;
   ratchet means substantially contained within said casing means;
   upper leg brace attachment means for fixedly securing said casing means to an upper leg brace associated with said orthopedic brace;
   lower leg brace attachment means for fixedly securing said casing means to a lower leg brace associated with said orthopedic brace; and
   selectably positionable ratchet control means for providing alternative operating characteristics to the joint so as to permit selective pivotal movement between said upper and lower leg braces, said alternative operating characteristics including (a) pivotal movement of the braces in one direction and locking of the braces against pivotal movement in the other direction; (b) pivotal movement of the braces in said other direction and locking of the braces against pivotal movement in said one direction; (c) pivotal movement of the braces both in said one direction and in said other direction; and, (d) locking of the braces against pivotal movement both in said one direction and in said opposite direction, wherein said upper leg brace attachment means includes a first extension means operably attachable to said ratchet means and being further fixedly secured to said upper leg brace associated with said orthopedic brace, and said lower leg brace attachment means includes a second extension means fixedly secured to said casing means associated with said ratchet means and being fixedly secured to said lower leg brace.

8. A kneejoint fitting for attachment to an orthopedic brace comprising:
   casing means;
   a ratchet wheel within said casing means, said ratchet wheel having a shaft portion extending from said casing means;
   first leg brace attachment means associated with the casing means for securing the casing means to one of an upper and lower leg brace member of an orthopedic brace;
   second leg brace attachment means associated with said shaft portion for securing said shaft portion to the other of said upper and lower leg brace member; and
   ratchet control means, including manual operating means on the exterior of the casing, for selectively controlling relative pivotal movement of the ratchet wheel and casing means, wherein the ratchet control means comprises first and second pawls within the casing means, and first and secondly manually operable levers for the respective pawls on the exterior of the casing means for selectively engaging and disengaging the pawls with the ratchet wheel so as to provide selective pivotal movement as between the wheel and casing means in one direction only, in the other direction only, in both directions, and to lock the ratchet wheel and casing means against relative pivotal movement in both said directions.

9. A fitting as defined in claim 8 wherein the first and second leg brace attachment means each comprises a pair of plates positionable on opposite sides of a respective brace member, and fastener means for securing the plate together.

* * * * *